United States Patent [19]
Perry

[11] Patent Number: 6,063,117
[45] Date of Patent: May 16, 2000

[54] POROUS ORBITAL IMPLANT STRUCTURE

[76] Inventor: Arthur C. Perry, 16418 La Via Feliz, Rancho Santa Fe, Calif. 92067-1102

[21] Appl. No.: 09/010,629

[22] Filed: Jan. 22, 1998

[51] Int. Cl.$^7$ ........................................................ A61F 2/14
[52] U.S. Cl. .................................................. 623/4; 623/11
[58] Field of Search ................................... 623/4, 11, 15; 433/173, 174

[56] References Cited

U.S. PATENT DOCUMENTS

| | | | |
|---|---|---|---|
| 2,688,139 | 9/1954 | Jardon | 623/4 |
| 4,321,711 | 3/1982 | Mano | 623/11 |
| 4,338,926 | 7/1982 | Kummer et al. | 623/16 |
| 4,925,924 | 5/1990 | Silver et al. | 530/356 |
| 4,976,731 | 12/1990 | Pery | 623/4 |
| 4,976,736 | 12/1990 | White et al. | 623/16 |
| 5,089,021 | 2/1992 | Vachet | 623/4 |
| 5,192,293 | 3/1993 | Cartwright et al. | 623/4 |
| 5,192,315 | 3/1993 | Jacob-LaBarre | 623/4 |
| 5,306,302 | 4/1994 | Bauer et al. | 623/11 |
| 5,326,356 | 7/1994 | Della-Valle et al. | 623/11 |
| 5,348,788 | 9/1994 | White | 623/11 |
| 5,433,996 | 7/1995 | Kranzler et al. | 623/11 |
| 5,466,258 | 11/1995 | Rubin | 623/4 |
| 5,556,427 | 9/1996 | Durette | 623/4 |
| 5,584,880 | 12/1996 | Martinez | 623/4 |
| 5,843,185 | 12/1998 | Leon-Rolden et al. | 623/4 |
| 5,856,367 | 1/1999 | Barrows et al. | 521/64 |
| 5,876,435 | 3/1999 | Swords et al. | 623/4 |
| 5,876,446 | 3/1999 | Agrawal et al. | 623/11 |

OTHER PUBLICATIONS

Alexander, H., et al., "Calcium–based Ceramics and Composites in Bone Reconstruction" *CRC Critical Reviews in Biocompatibility* (1987) 4:43–77.

Baird, A., and Bohlen, P., "Fibroblast Growth Factors", In: Sporin, M. B., and Roberts, A.B., eds. *Peptide Growth Factors and Their Receptors* 1. (New York, Springer–Verlag, 1991).

Baumgarten, D., et al., "Evaluation of Biomatrix Hydroxyapatite Ocular Implants with Technetium–99m–mdp" *J Nucl Med* (1993) 34:467–468.

Buettner, H. and Bartley, G., "Tissue Breakdown and Exposure Associated with Orbital Hydroxyapatite Implants" *Am J Ophthalmol* (1992) 113:669–673.

Cutler N. L., "A Positive Contact Ball and Ring Implant for Use after Enucleation" *Arch Ophthal* (1947) 37:73–81.

DePotter, P., et al., "Role of Magnetic Resonance Imaging in the Evaluation of the Hydroxyapatite Orbital Implant" *Ophthalmology* (1992) 99:824–830.

Durham D. G., "The New Ocular Implants" *Am J Ophthalmol* (1949) 32:79–89.

Dutton, J. J., "Coralline Hydroxyapatite as an Ocular Implant" *Ophthalmology* (1991) 98:370–7.

(List continued on next page.)

*Primary Examiner*—Gene Mancene
*Assistant Examiner*—Eduardo C. Robert
*Attorney, Agent, or Firm*—Henri J. A. Charmasson; John D. Buchaca

[57] ABSTRACT

A porous structure for implantation into the orbital cavity of a mammal who has had an ocular enucleation, evisceration or who needs to have an orbital implant replaced, the structure comprising pores having a mean size of less than 200 micrometers. Also disclosed is a surgical method for placing an implant into a mammal who has had an ocular enucleation, evisceration or who needs implant replacement, whereby the implant obtains rapid ingrowth of connective and vascular tissues. The method comprises: selecting a porous ocular implant comprising pores with a mean size of less than 200 micrometers; and, placing the implant into an orbital cavity of a mammal.

19 Claims, 12 Drawing Sheets

OTHER PUBLICATIONS

Ferrone, P.J., and Dutton, J.J., "Rate of Vascularization of Coralline Hydroxyapatite Ocular Implants" *Ophthalmology.* (1992) 99:376–379.

Folkman, J., and Klagsbrun, M., "Angiogenic Factors" *Science* (1987) 235:442–447.

Geist, C.E., et al., "Orbital Augumentation by Hydroxylapatite–based Composites. A Rabbit Study and Comparative Analysis" *Ophthalmic Plast Reconstr Surg* (1991) 7:8–22.

Gougelmann, H. P., "The Evolution of the Ocular Motility Implant" *Int Ophthalmol Clin* (1976) 10:689–711.

Klawitter, J.J., An Evaluation Bone Growth into Porous High Density Polyethylene *J. Biomed. Mater Res.* 10:311–323 (1976).

Merritt, K., et al., "Implant Site Infection Rates with Porous and Dense Materials" *J Biomed Mater Res* (1979) 13:101–8.

Montesano, R., et al., "Basic Fibroblast Growth Factor Induces Angiogenesis In Vitro" *Proc Natl Acad Sci USA* (1986) 83:7297–7301.

Mules, P. H., "Evisceration of the Globe, with Artificial Vitreous" *Trans Ophthalmol Soc UK* (1885) 5:200–206.

Peltier, L. F., "The Use of Plaster of Paris to Fill Defects in Bone" *Clin Orthop* (1961) 21:1–31).

Perry, A. C., "Integrated Orbital Implants" *Adv Ophthalmic Plast Reconstr Surg* (1990) 8:75–81.

Rieck, P., et al., "Recombinant Human Basic Fibroblast Growth Factor (Rh–$\beta$FGF) in Three Different Wound Models in Rabbits: Corneal Wound Healing Effect and Pharmacology" *Exp Eye Res* (1992) 54:987–998.

Rieck, P., et al., "Human Recombinant $\beta$FGF Stimulates Endothelial Wound Healing in Rabbits." *Current Eye Research* (1992) 11:1161–1172.

Rosen, H. M., "The Response of Porous Hydroxyapatite to Contiguous Tissue Infection" *Plast Recontr Surg* (1991) 88:1076–80.

Rubin, P. A. D., et al. "Comparison of Fibrovascular Ingrowth Into Hydroxyapatite and Porous Polyethylene Orbital Implants" *Ophthalmic Plastic and Reconstructive Surgery* 10(2):96–103 (1994).

Ruedemann A. D., "Plastic Eye Implant" *Amer J Ophthalmol* (1946) 29:947–952.

Shields, C. L., et al, "Lack of Complications of the Hydroxyapatite Orbital Implant in 250 Consecutive Cases" *Trans Am Ophthalmol Soc* (1993) 91:177–189; discussion 189–95.

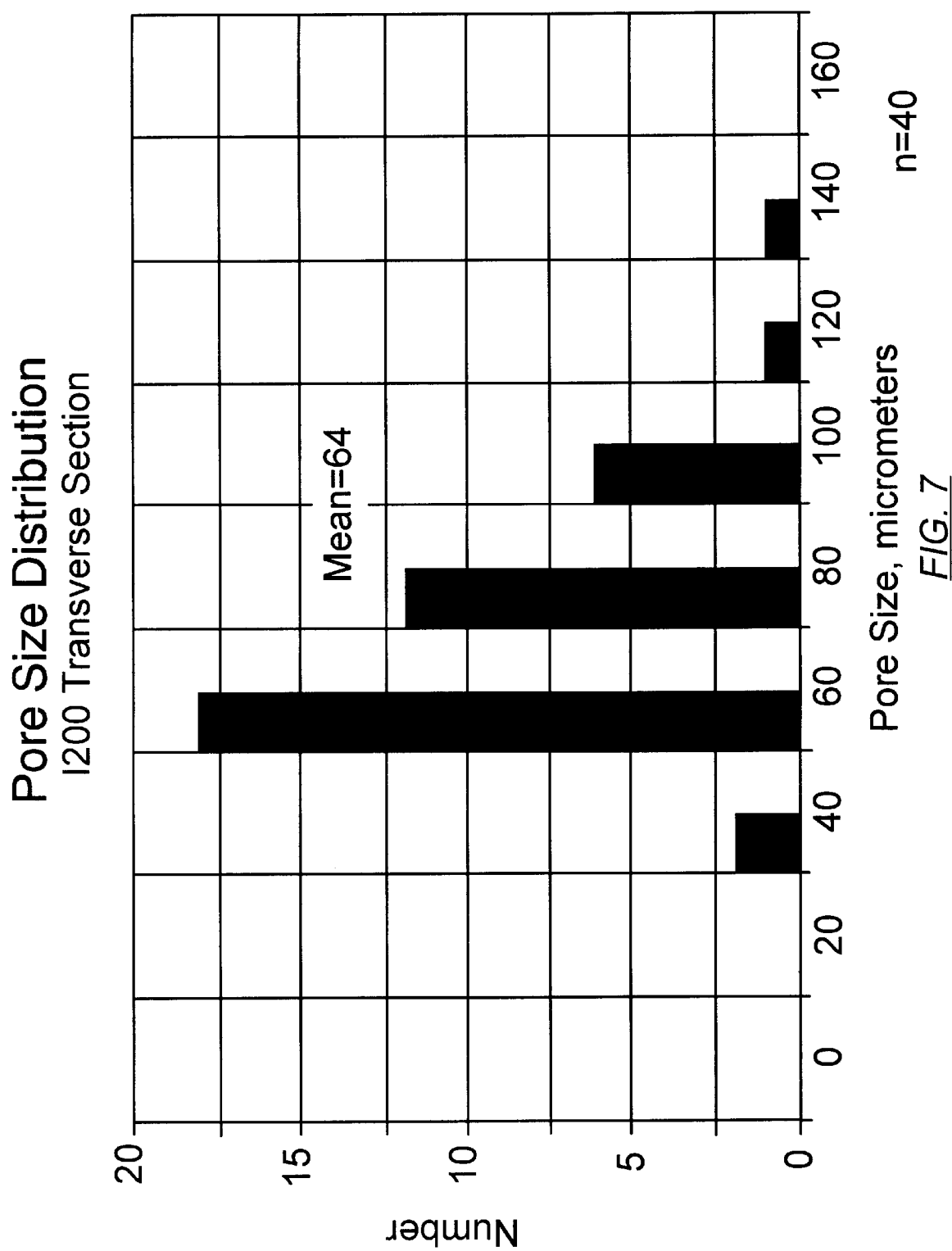

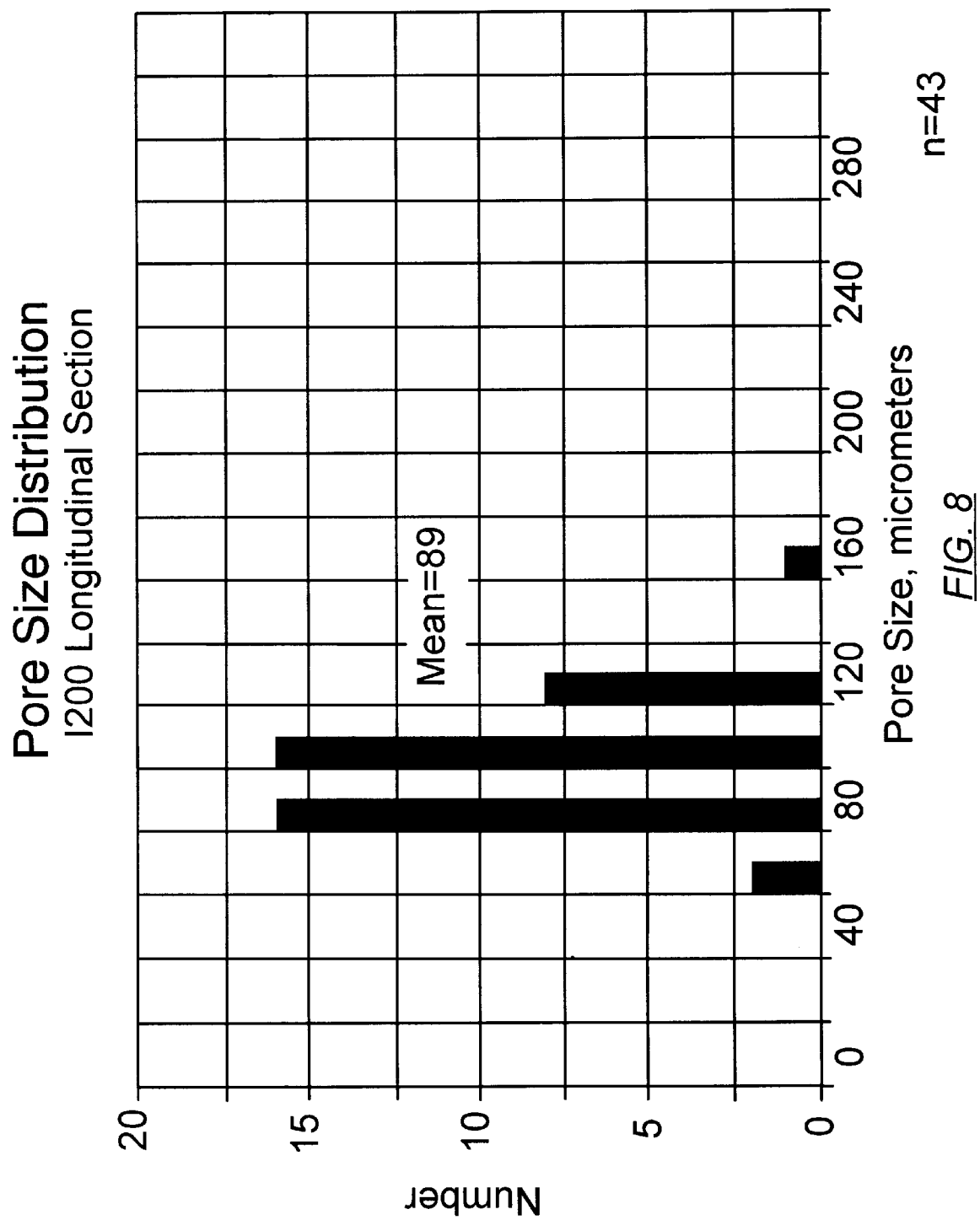

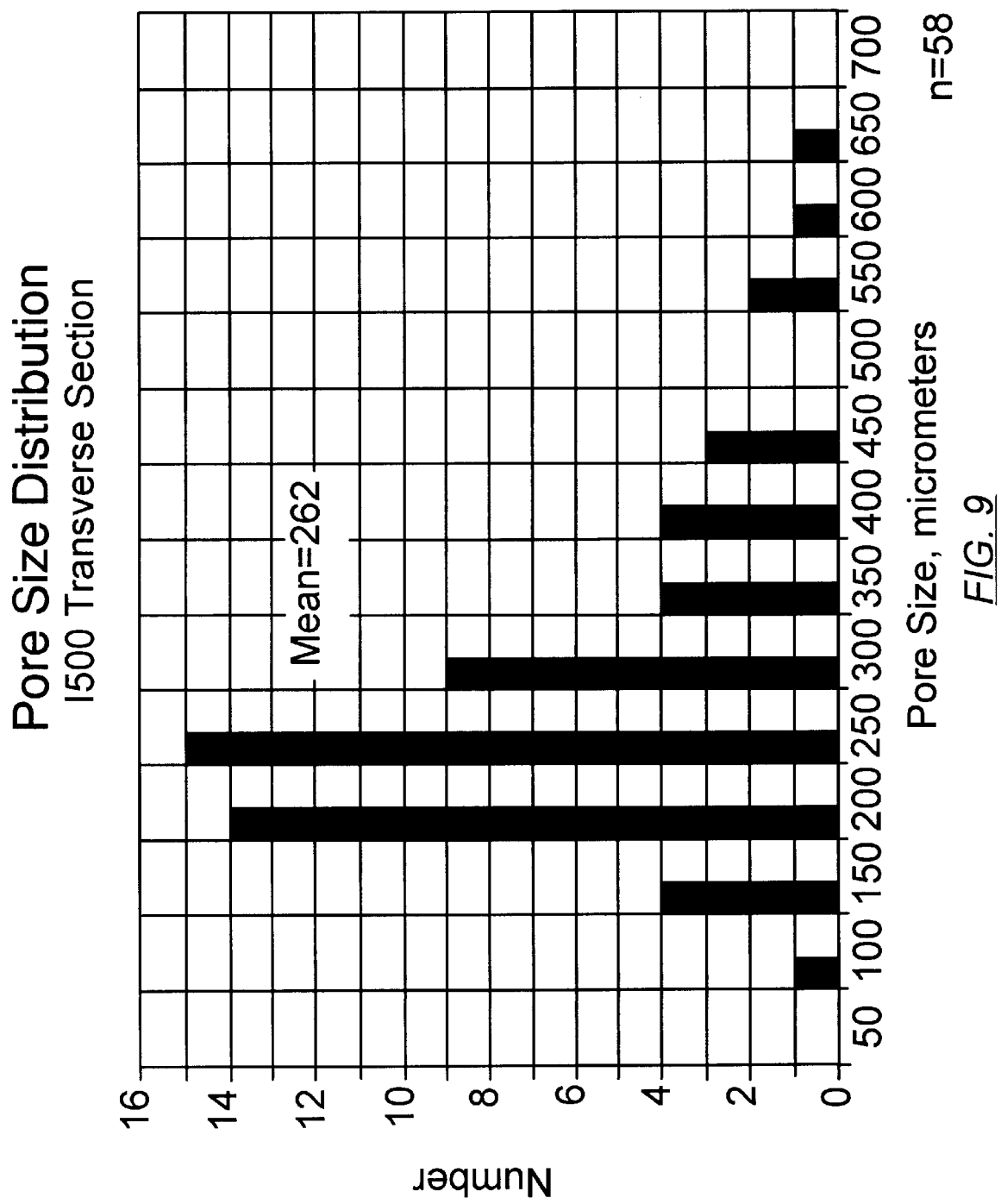

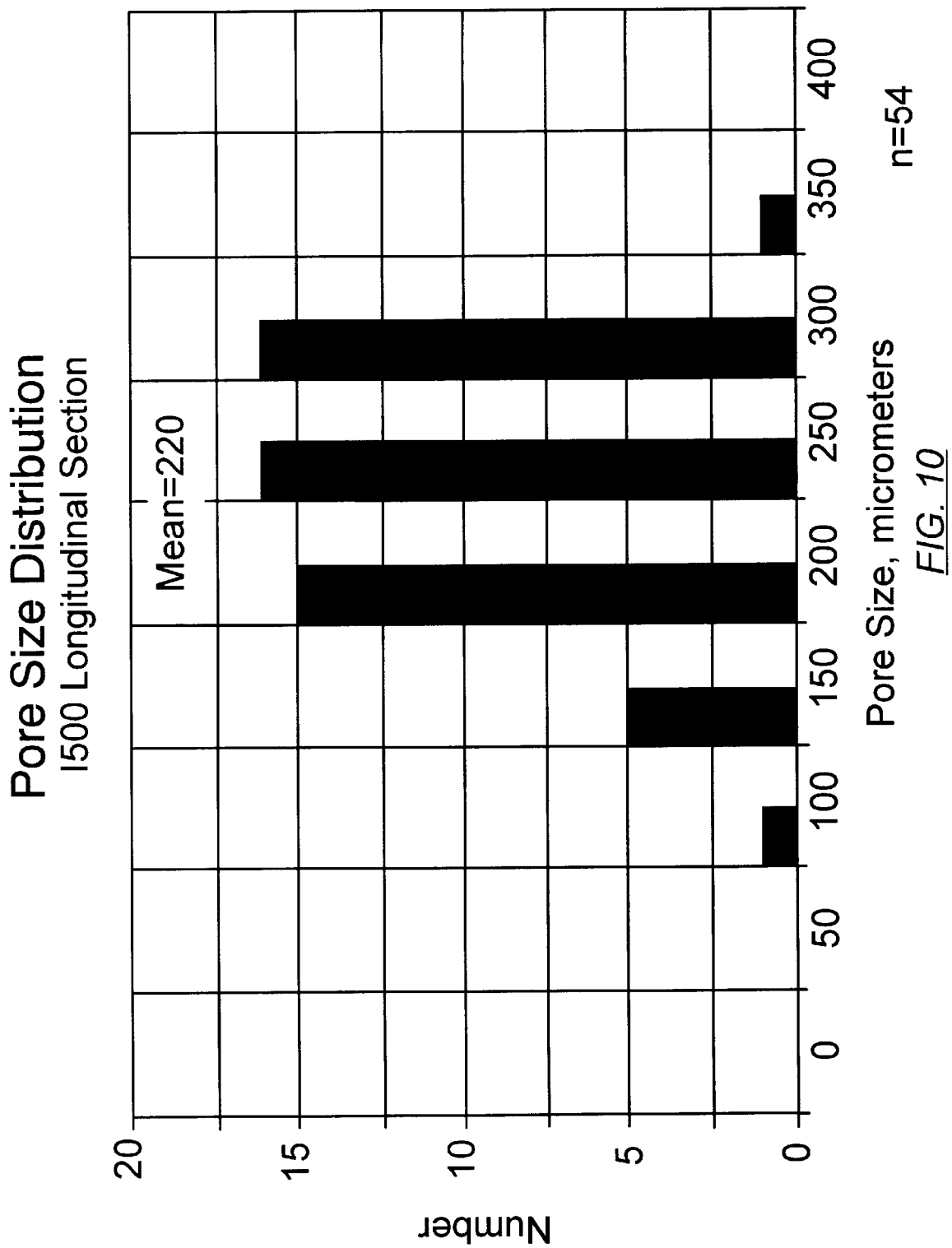

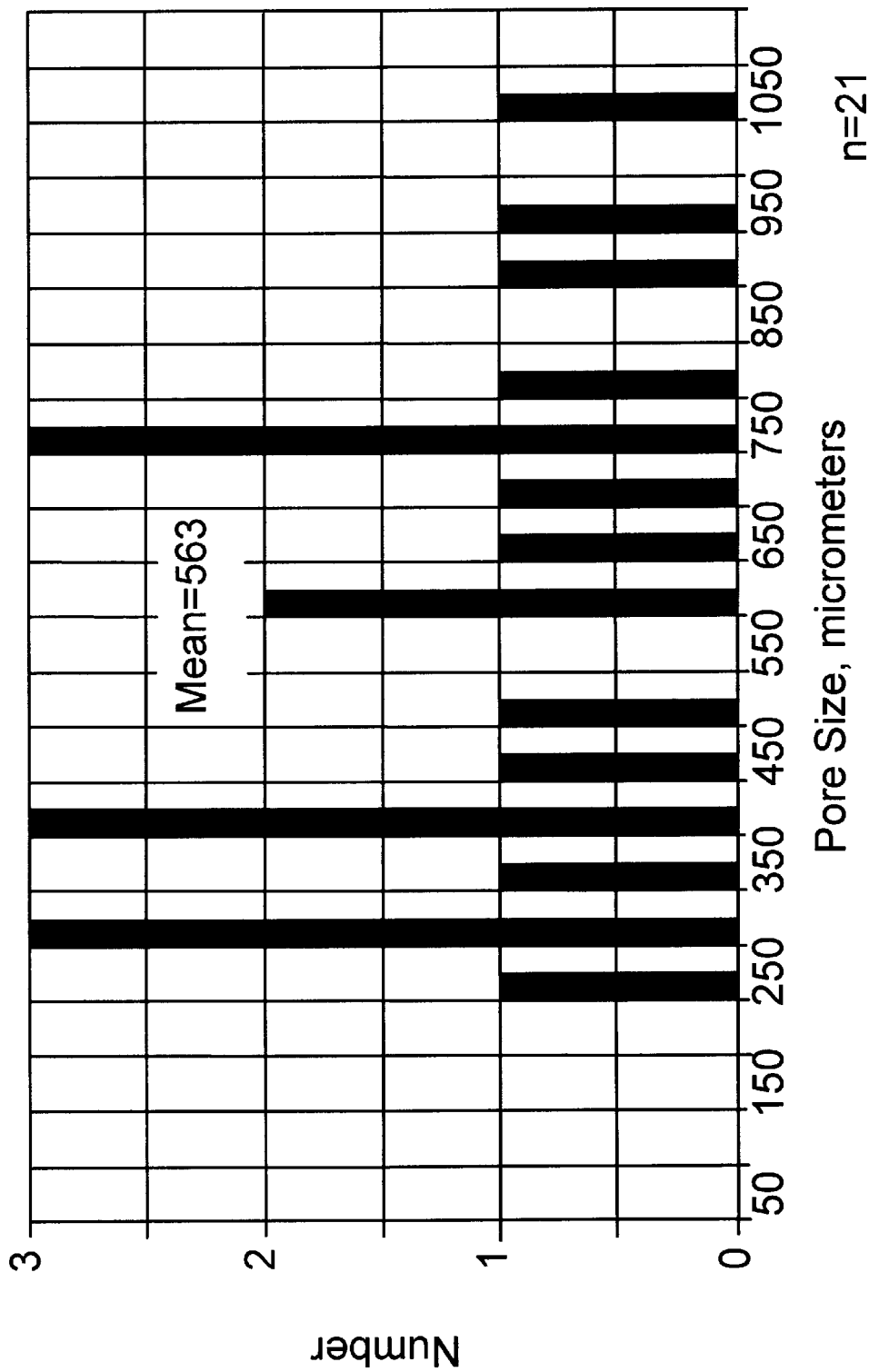

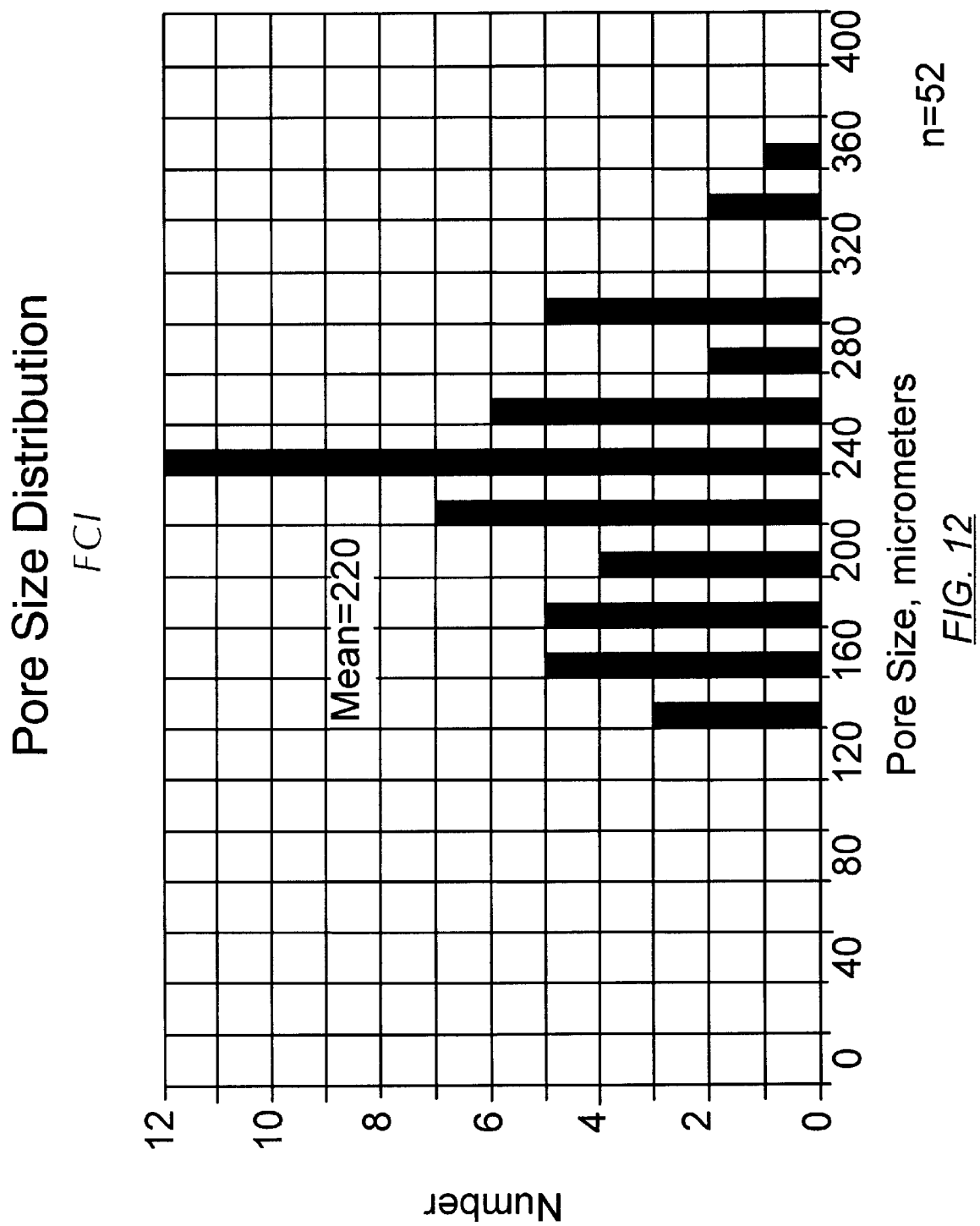

POROUS ORBITAL IMPLANT STRUCTURE

FIELD OF THE INVENTION

This invention concerns biocompatible compositions of matter. More particularly, it concerns an ocular implant capable of rapid and effective fibrovascular integration of vascular and/or connective tissues following implantation into the orbital cavity of an anophthalmic mammal.

BACKGROUND ART

Since at least 1884, surgeons have sought a means to improve the cosmetic rehabilitation of the anophthalmic patient. Accordingly, improvements have been sought by increasing the support of the artificial eye and by attempts to transfer all latent muscle movement directly to the artificial eye via some form of direct coupling between the eye and the implant. (Ruedemann A. D., "Plastic Eye Implant" *Amer J Ophthalmol* (1946) 29:947–952).

Ocular implants are used to replace the volume lost after enucleation or evisceration to improve the cosmetic psychological and rehabilitation of the anophthalmic patient. Many materials have been used for this purpose, starting with Mules's hollow glass spheres in 1884. (Mules, P. H., "Evisceration of the Globe, with Artificial Vitreous" *Trans Ophthalmol Soc UK* (1885) 5:200–206) Mules employed a hollow glass sphere; this sphere offered some support for the upper eyelid but was unable to relieve the chronic downward pressure on the lower lid. (Id.) It is necessary to avoid chronic downward pressure on the lower lid to alleviate the lid sag characteristic of long-term anophthalmic patients. (Ruedemann A. D., "Plastic Eye Implant" *Amer J Ophthalmol* (1946) 29:947–952, Durham D. G., "The New Ocular Implants" *Am J Ophthalmol* (1949) 32:79–89).

Numerous implant innovations followed Mules' implant, including implants composed of: gold, cartilage, fat, fascia lata, bone, xenogeneic animal eyes, silver, Vitallium, platinum, aluminum, sponge, wool, rubber, silk, catgut, peat, agar, asbestos, cork, ivory, paraffin, Vaseline, celluloid, and silicone. For example, silicone implants have included spheres of various designs, including those which are solid, hollow, and inflatable. Glass beads have also been used to fill irregular cavities in the orbit (Gougelmann, H. P., "The Evolution of the Ocular Motility Implant" *Int Ophthalmol Clin* (1976) 10:689–711). Most of the implants composed of these materials were fully buried in the orbit, which was the usual procedure prior to 1941. (Gougelmann, H. P., "The Evolution of the Ocular Motility Implant" *Int Ophthalmol Clin* (1976) 10:689–711).

In 1941, a combined implant and acrylic prosthesis was introduced by Ruedemann (Ruedemann, A. D., "Plastic Eye Implant" *Amer J Ophthalmol* (1946) 29:947–952). The extraocular muscles were attached to the posterior portion of this implant, which was covered with gauze. This Ruedemann implant was eventually abandoned, since it had to be manufactured before each operation, and further because secondary strabismus procedures were often required to correct late position problems. This implant was partially exposed and partially buried.

There have been many other design variations of orbital implants since the Ruedemann eye, including several implants that when placed were partially exposed and partially buried, these implants allowed "interaction" with an externally placed, contact lens-type artificial eye through some exposed means, such as pegs, pins, or screws (Gougelmann, H. P., "The Evolution of the Ocular Motility Implant" *Int Ophthalmol Clin* (1976) 10:689–711).

These partially exposed implants imparted good motility to the artificial eye, but were prone to infection and extrusion. Buried implants were then developed to provide motility through special contours on the anterior aspect of the implant which matched corresponding contours on the posterior aspect of the eye. Other buried implants employed magnets to achieve a form of coupling between the implant and the eye.

Cutler employed a prosthesis comprising an implant with a peg to completely support the weight of the artificial eye and transfer all latent movement to the eye; however, these Cutler prostheses resulted in high rates of infection due to the inability of the material from which the implant was formed to support robust wound closure at the peg-implant interface. (Cutler M. L., "A Positive Contact Ball and Ring Implant for Use after Enucleation" *Arch Ophthal* (1947) 37:73–81).

In recent years, porous ocular implants composed of hydroxyapatite (HA) and porous polyethylene (PP) have become accepted alternatives to traditional, nonporous spheres composed of silicone or acrylic.

There is some variation in the art concerning the term "integration". The term is used to denote any connection between tissues of the recipient and the implant (e.g. suturing an extraocular muscle to a wire loop). However, as used in the context of the present invention, integrated implants are porous implants capable of sustaining fibrovascular in growth. Porous implants have the advantage of becoming infiltrated by fibrovascular tissue, thereby providing resistance to infection, migration, and extrusion. (Merritt, K., et al., "Implant Site Infection Rates with Porous and Dense Materials" *J Biomed Mater Res* (1979) 13:101–8; Rosen, H. M., "The Response of Porous Hydroxyapatite to Contiguous Tissue Infection" *Plast Recontr Surg* (1991) 88:1076–80; Dutton, J. J., "Coralline Hydroxyapatite as an Ocular Implant" *Ophthalmology* (1991) 98:370–7; Shields, C. L, et al., "Lack of Complications of the Hydroxyapatite Orbital Implant in 250 Consecutive Cases" *Trans Am Ophthalmol Soc* (1993) 91:177–189; discussion 189–95).

An integrated implant also offers the possibility of good motility for an artificial eye by use of a motility/support peg. Furthermore, an integrated implant that incorporates a motility/support peg may (by supporting the artificial eye) also help prevent the development of a deep superior sulcus and entropion or ectropion of the lower lid, and may reduce other long-term structural defects due to chronic weight and pressure from the artificial eye. (Gougelmann, H. P., "The Evolution of the Ocular Motility Implant" *Int Ophthalmol Clin* (1976) 10:689–711).

Not all porous implants can transfer implant movement directly to the artificial eye via a motility/support peg. Porous HA implants have the ability to accept a motility/support peg because, when fully vascularized, they can support complete epithelialization of the internal surfaces of the peg hole, thereby sealing the implant from the external environment and preventing infection. Porous polyethylene has only recently been coupled to the eye in this manner. Generally, porous polyethylene implants impart some motility through movement of the fornices, when the extraocular muscles are surgically connected to the fornices or to the implant.

Vascularization can be a lengthy process in porous implants, requiring 6 to 10 months or longer in some cases (Dutton, J. J., "Coralline Hydroxyapatite as an Ocular Implant" *Ophthalmology* (1991) 98:370–7). Peg placement is usually delayed until the implant shows a high degree of fibrovascular ingrowth, as established by some objective means, such as a bone scan or MRI. (Baumgarten, D., et al., "Evaluation of Biomatrix Hydroxyapatite Ocular Implants with Technetium-99m-mdp" *J Nucl Med* (1993) 34:467–468; DePotter, P., et al., "Role of Magnetic Resonance Imaging in the Evaluation of the Hydroxyapatite Orbital Implant" *Ophthalmology* (1992) 99:824–830) Since drilling of the implant for placement of the motility/support peg is usually delayed until the implant is fully vascularized, the complete rehabilitation of the patient can be limited by the speed and degree of fibrovascular ingrowth. Therefore, rapid, complete vascularization of these implants is desirable. Previous efforts to speed the process have included drilling holes in HA implants (Ferrone, P. J., and Dutton, J. J., "Rate of Vascularization of Coralline Hydroxyapatite Ocular Implants" *Ophthalmology*. (1992) 99:376–379) and cutting windows in any coating materials, such as donor sclera, used to wrap the implant, in order to increase direct contact between the HA material and the highly vascular tissues of the orbit.

In particular, porous HA implants have the known ability to accept a motility/support peg, making possible the direct transfer of implant movement to the artificial eye. Preferred support pegs include those such as disclosed in copending application Ser. No. 08/241,960, filed May 12, 1994; Ser. No. 08/853,647 filed May 9, 1997; and, Ser. No. 08/886,600 filed Jul. 1, 1997, each in the name of Arthur C. Perry, and each of which are fully incorporated by reference herein.

Since the cosmetic and psychological rehabilitation of the anophthalmic patient may depend on life-like movement and position of an artificial eye, compositions and methods are needed to increase the speed of fibrovascular ingrowth into an implant, since such ingrowth is a precondition of drilling the implant to accept the motility/support peg.

Popular coralline HA implants currently available have a reported pore size of 500 µm (HA500) (Interpore 500, Interpore International, Irvine, Calif.); these implants provide excellent fibrovascular ingrowth, but have a rough outer surface that may lead to exposure of the implant following surgery, due to abrasion of the overlying conjunctiva and Tenon's capsule. To avoid implant exposure, current practice calls for coating the implant in some material, such as donor sclera or fascia lata. (Perry, A. C., "Integrated Orbital Implants" *Adv Ophthalmic Plast Reconstr Surg* (1990) 8:75–81). However, concerns about HIV infection and the additional surgeries needed to harvest a donor coating material have led to a search for suitable alternative coatings. (Dutton, J. J., "Coralline Hydroxyapatite as an Ocular Implant" *Ophthalmology* (1991) 98:370–7). Accordingly, there is a need for an ocular implant material having a smoother implant surface. A smoother implant surface could reduce abrasion on the orbital tissues during and after implantation, facilitates deeper placement of the implant in the orbit, and can reduce intraoperative time because the implant may not need to be surrounded by an additional coating.

It has been found that both hydroxyapatite and porous polyethylene implants are capable of complete vascularization. The hydroxyapatite implants vascularize more rapidly than the commercially available porous polyethylene (MedPor, Porex Surgical, College Park, Ga.). When the interstitial pore size of the PP was increased to a reported pore size of approximately 400 microns, which corresponded to the reported pore size of commercially available HA (e.g., Interpore, Irvine, Calif.), the rate and extent of vascularization of PP and HA were more similar, a is finding that indicated that increasing the interstitial pore size favorably influenced vascularization of porous implants. (Rubin, P. A. D., et al. "Comparison of Fibrovascular Ingrowth Into Hydroxyapatite and Porous Polyethylene Orbital Implants" *Ophthalmic Plastic and Reconstructive Surgery* 10(2):96–103 (1994)).

Thus, it was found that PP with pore sizes in the 400 micron range, resulted in more optimal orbital tissue ingrowth than a denser PP implant having an interstitial pore size of approximately 150 microns. It was noted by the authors of the previous study that it was not clear to what extent a further increases in pore size would enhance vascularization, providing guidance in the art that even larger pore sizes were desirable. Again, it was noted that there was a need for maximizing the rate and extent of fibrovascular ingrowth, while minimizing the inflammation and the potential for infection with the relatively large orbital implant. Maximized soft tissue ingrowth into the depths of an implant decreases the inflammatory cell response and potential for infection. (Rubin, P. A. D., et al. "Comparison of Fibrovascular Ingrowth Into Hydroxyapatite and Porous Polyethylene Orbital Implants" *Ophthalmic Plastic and Reconstructive Surgery* 10(2):96–103 (1994)).

Plaster of Paris is a biocompatible material which is composed of the hemihydrate form of calcium sulfate produced by heating gypsum calcium sulfate dihydrate to drive off water. (Alexander, H., et al., "Calcium-based Ceramics and Composites in Bone Reconstruction" *CRC Critical Reviews in Biocompatibility* (1987) 4:43–77) It is highly biocompatible and has been successfully used to fill defects in bone (Peltier, L. F., "The Use of Plaster of Paris to Fill Defects in Bone" *Clin Orthop* (1961) 21:1–31), in dental surgery, and for orbital augmentation (Geist, C. E., et al., "Orbital Augmentation by Hydroxylapatite-based Composites. A Rabbit Study and Comparative Analysis" *Ophthalmic Plast Reconstr Surg* (1991) 7:8–22). When mixed with HA particles for orbital augmentation, calcium sulfate has been shown to resorb within several weeks of implantation. Moreover, connective tissue ingrowth has been noted in mixtures of HA and calcium sulfate, with minimal inflammation (Geist, C. E., et al., "Orbital Augmentation by Hydroxylapatite-based Composites. A Rabbit Study and Comparative Analysis" *Ophthalmic Plast Reconstr Surg* (1991) 7:8–22).

Thus, there is need for an orbital implant with as many of the following characteristics as possible: It should be biocompatible, readily vascularized, and have little or no tendency toward extrusion, migration, or infection (see, e.g., Dutton, J. J., "Coralline Hydroxyapatite as an Ocular Implant" *Ophthalmology* (1991) 98:370–7); it should also serve to impart motility to an artificial eye while supporting the weight of the eye to preserve the delicate, and cosmetically important, structures of the lid; and preferably is capable of being attached to an artificial eye.

DISCLOSURE OF THE INVENTION

A porous structure for implantation into the orbital cavity of a mammal comprising pores having a mean size of less than 200 micrometers. In preferred embodiments, the pores have a mean size of from 50 to 150 micrometers; a mean size of from 60 to 90 micrometers; a mean size of from 75 to 85 micrometers; or, a mean size of about 77 micrometers. The structure can comprise a growth factor, such as recombinant human basic fibroblast growth factor beta. The structure can comprise a biocompatible coating, such as calcium sulfate, polylactic acid, polyglycolic acid, or animal tissue.

Also disclosed is a surgical method for placing a implant into a mammal who has had an ocular enucleation, evisceration or who needs implant replacement (i.e. "secondary implantation"), whereby the implant obtains rapid ingrowth of connective and vascular tissues, said method comprising: selecting a porous ocular implant comprising pores with a mean size of less than 200 micrometers; and, placing the implant into an orbital cavity of a mammal. The method can further comprise a step of burying the implant beneath conjunctival tissues of the mammal. The method can further comprise a step of covering the implant before the placing step, with a material such as scleral tissue or calcium sulfate. The method can further comprise applying a growth factor to the implant, such as recombinant human basic fibroblast growth factor beta.

DESCRIPTION OF FIGURES

FIG. 7 depicts a histogram of pore size measurements for transverse sections of the HA 200 samples.

FIG. 8 depicts a histogram of the pore size measurements from longitudinal sections of the HA 200 implants.

FIG. 9 depicts a histogram for the pore size measurements of HA 500 implants taken along transverse sections.

FIG. 10 depicts a histogram of pore size measurements taken from longitudinal sections of HA 500 implants.

FIG. 11 depicts a histogram of pore size measurements for the implants of porous polyethylene.

FIG. 12 depicts a histogram for the pore size measurements taken from synthetic hydroxyapatite implants.

MODES FOR CARRYING OUT INVENTION

As disclosed herein, fibrovascular ingrowth into various porous ocular implants was investigated in an animal model, as a function of implant material composition, porosity, addition of growth factors, and use of coatings. Eighty-one new Zealand white rabbits underwent unilateral enucleation and implantation with ocular implants composed of the following materials:

coralline hydroxyapatite (HA) ("HA200") (Interpore 200, Interpore International, Irvine, Calif.);

coralline hydroxyapatite ("HA500") (Interpore 500, Interpore International, Irvine, Calif.);

synthetic HA ("synHA"); and, high-density porous polyethylene ("PP").

The HA200, HA500, and PP implants were implanted untreated or after treatment with recombinant human basic fibroblastic growth factor (Rh-$\beta$FGF). Nine HA500 implants were implanted after coating with calcium sulfate (Plaster of Paris) to provide a smooth outer surface. Implants were harvested at 1-, 2-, 4-, or 8-week intervals and were examined histologically.

As discussed below, no significant differences in the degree of fibrovascular ingrowth were found as a function of implant composition. Surprisingly, significant increases in ingrowth were found in HA200 compared with HA500 implants. Increases in ingrowth were also found in Rh-$\beta$FGF-treated implants compared with untreated controls. The calcium sulfate coated implants showed less vascularization compared with the uncoated implants, although the difference was not significant.

Composition

Figure 3:
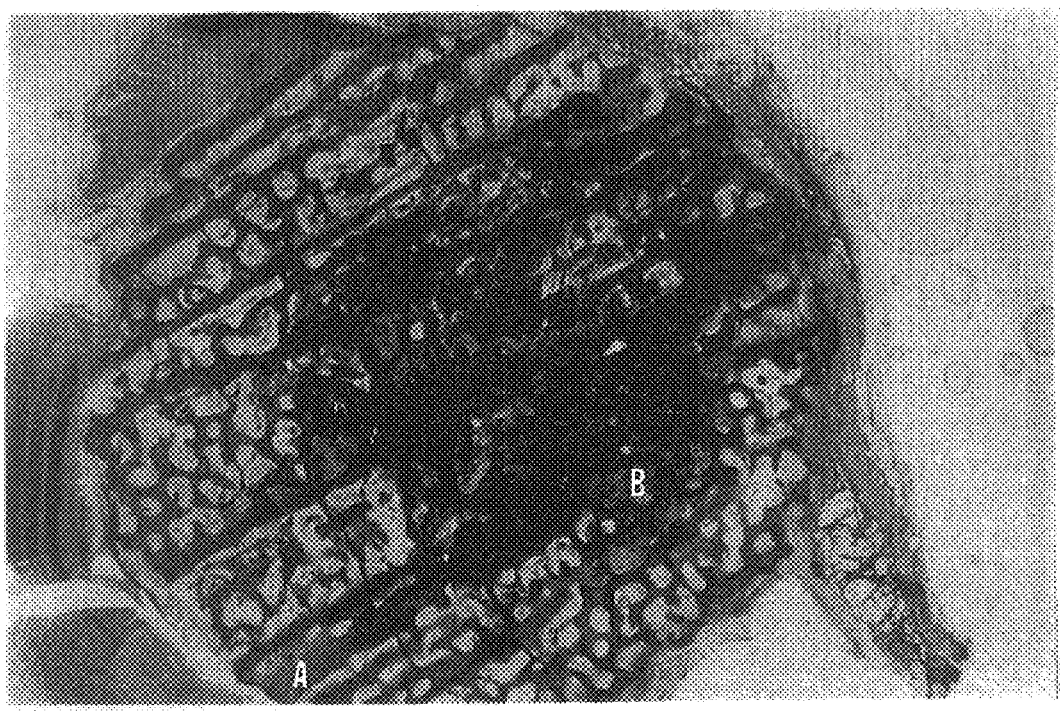
FIG. 3. Cross-sectional specimen of HA500 explanted four weeks postoperatively. A, hydroxyapatite material; B, pore area. Note robust fibrovascular ingrowth into pore area. This specimen was graded $\leq 100\%$ ingrown.
Figure 4:
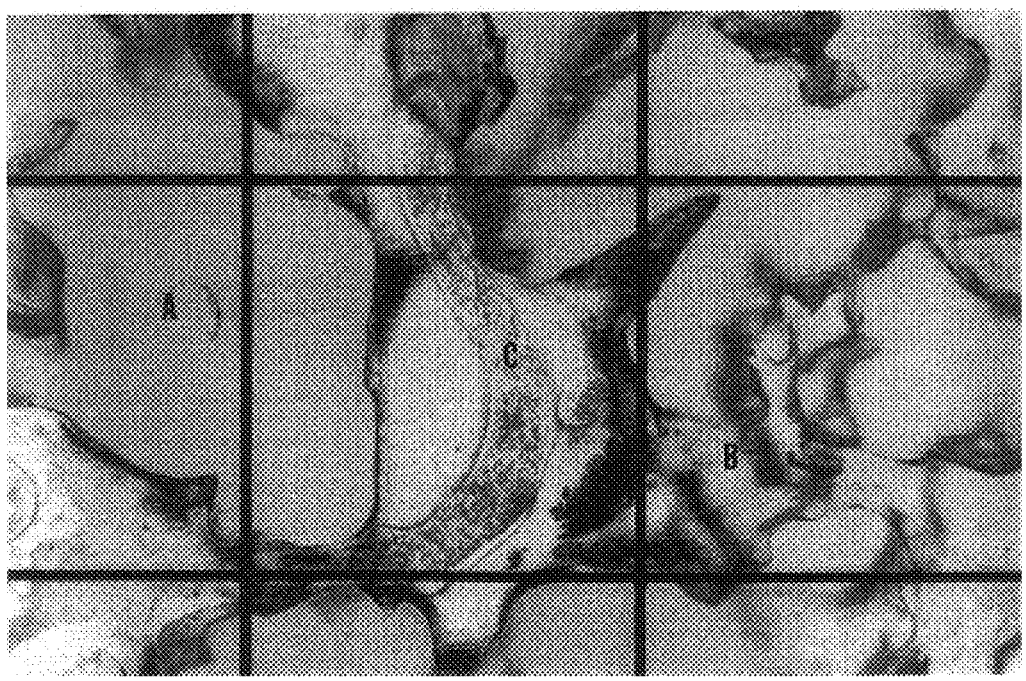
FIG. 4. Cross-sectional specimen of porous polyethylene explanted eight weeks postoperatively. A, polyethylene material; B, pore area containing fibrous tissue; C, pore are containing a vessel. Note the presence of both fibrous and vascular tissue. This specimen was graded $\leq 100\%$ ingrown.

The two most popular materials used to manufacture porous implants, i.e., implants of PP and implants of coralline HA, were tested in the studies disclosed herein. Also, tested was synthetic hydroxyapatite. No significant differences in ingrowth were noted between implants composed of these materials (FIGS. 3 and 4), although they represent markedly different technologies.

Porosity

Porous implant materials, such as HA and PP, possess many of the characteristics presently deemed preferred for an ocular implant, and they offer clear advantages over solid, nonporous spheres. These preferred porous compositions allow fibrovascular tissue to grow into the implants; the presence of fibrovascular ingrowth is believed to prevent migration within the orbit and may help to minimize the chance of infection and exposure through breakdown of the thin overlying tissues of the conjunctiva and Tenon's capsule (Buettner, H. and Bartley, G., "Tissue Breakdown and Exposure Associated with Orbital Hydroxyapatite Implants" *Am J Ophthalmol* (1992) 113:669–673). A further advantage of porous implants is their ability to be directly integrated with the extraocular muscles, thereby maximizing the transfer of all latent muscle movement to the implant.

The importance of pore size in determining the nature of fibrovascular tissue was investigated in the present study. It was a surprising finding that the HA200 showed significantly better ingrowth than HA500. This result is believed to be due to the fact that smaller pores, in this case pores reported as 200-$\mu$m, rather than pores reported as 500-$\mu$m, may encourage fibrovascular ingrowth. This is a clinically important finding, for an additional reason: HA200 implants have a smoother surface and may thus be less prone to abrade the overlying tissues and are less likely to lead to exposures. It may also be easier to place these implants more deeply within the orbit.

Growth Factors

Growth factors have been successful in associated medical fields, and relatively recently have been used in ophthalmology. Thus, the present studies were performed to determine the applicability of growth factors in ocular implant surgery. Traditional methods of extracting growth factors from human placenta or bovine brain were laborious and ineffective (Rieck, P., et al., "Human Recombinant $\beta$FGF Stimulates Endothelial Wound Healing in Rabbits."

Current Eye Research (1992) 11:1161–1172); but recent progress in recombinant DNA technology has made it possible to produce growth factors on a scale large enough to make their therapeutic use a practical consideration.

Basic fibroblast growth factor (FGF) is stored within basement membranes and may exhibit angiogenic activity. Recombinant human basic fibroblast growth factor is derived from E. coli through recombinant DNA techniques. Rh-βFGF is a 146 amino acid polypeptide from a family of growth factors that show a high affinity for heparin and have been extracted from a number of tissues such as eye, retina, brain, pituitary, and human placenta (Folkman, J., and Klagsbrun, M., "Angiogenic Factors" Science (1987) 235:442–447; Rieck, P., et al., "Recombinant Human Basic Fibroblast Growth Factor (Rh-βFGF) in Three Different Wound Models in Rabbits: Corneal Wound Healing Effect and Pharmacology" Exp Eye Res (1992) 54:987–998). It is one of several angiogenic factors which in recent years have been fully purified, their amino acid sequences determined, and their genes cloned.

Recombinant human fibroblast growth factor beta (Rh-βFGF) has been used in rabbit corneal studies to promote epithelial and endothelial wound healing (Rieck, P., et al., "Human Recombinant βFGF Stimulates Endothelial Wound Healing in Rabbits." Current Eye Research (1992) 11:1161–1172).

Rh-βFGF was used in the present study because of the demonstrated ability of this and related growth factors to induce new capillary blood vessel ingrowth in vitro and in vivo (Montesano, R., et al., "Basic Fibroblast Growth Factor Induces Angiogenesis In Vitro" Proc Natl Acad Sci USA (1986) 83:7297–7301; Baird, A., and Bohlen, P., "Fibroblast Growth Factors", In: Sporin, M. B., and Roberts, A. B., eds. Peptide Growth Factors and Their Receptors 1. (New York, Springer-Verlag, 1991). Capillary blood vessel formation is a complex process which includes endothelial cell proliferation, the sprouting of new capillaries, the migration of endothelial cells, and the breakdown of extracellular matrix surrounding existing capillaries.

Exogenously applied Rh-βFGF may stimulate all of the biological activities required to elicit neovascularization (Rieck, P., et al., "Human Recombinant βFGF Stimulates Endothelial Wound Healing in Rabbits." Current Eye Research (1992) 11:1161–1172).

The present studies investigated whether Rh-βFGF could be affixed to PP and HA implants and, if so, whether they would enhance the rate of vascularization.

Figure 5:
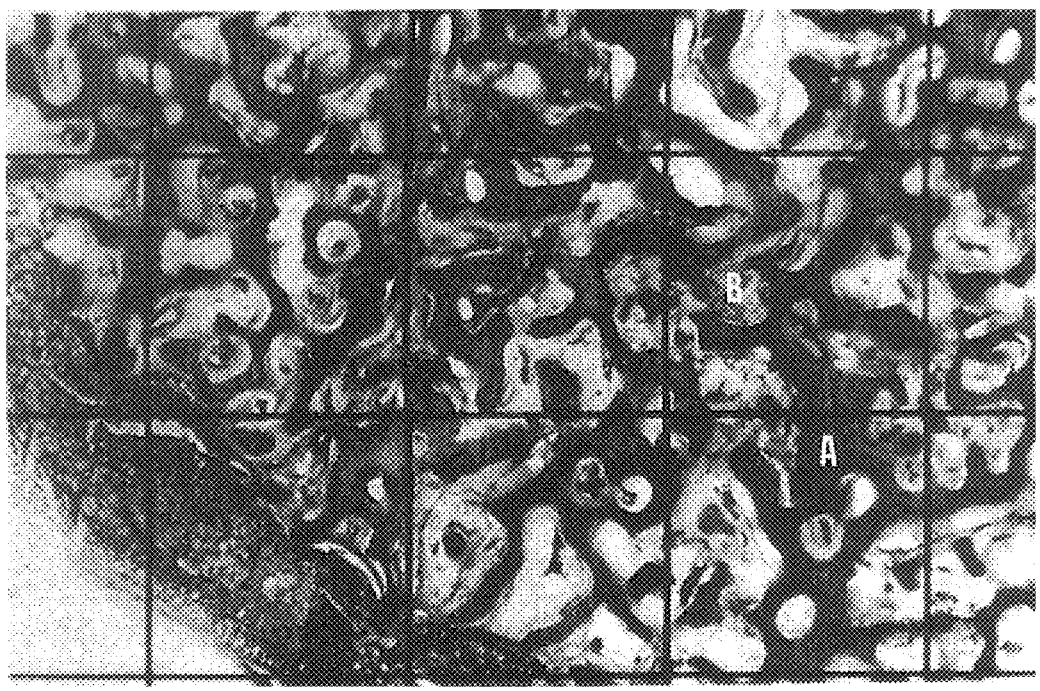
FIG. 5. Cross-sectional specimen of growth factor-treated HA200 explanted four weeks postoperatively. A, hydroxyapatite material; B, pore area containing fibrovascular tissue. Note the direct apposition to the implant of highly vascular orbital tissue. This specimen was graded $\leq 100\%$ ingrown.

In the present studies, all implants treated with Rh-βFGF showed significant increases in fibrovascular ingrowth compared with identical, untreated implants (FIG. 5). This finding is clinically significant, in view of the objective to decrease the latency of peg-fitting following enucleation, evisceration, or secondary implantation. It is also noteworthy that none of the implants treated with Rh-βFGF in the present studies were observed to be exposed at any time, despite marked postoperative inflammation in orbits containing these implants.

Although previous corneal studies showed that Rh-βFGF is tolerated in rabbits, a greater-than-normal inflammatory response was observed during the first 72 hours, characterized by increased erythema and orbital/peri-orbital edema. However, there were no episodes of extrusion or infection, and by 72 hours the rabbits showed no unusual symptoms. As appreciated by one of ordinary skill in the art, this finding suggests that the Rh-βFGF did bind to some degree to the implants and that a lower dose might be used in any future situations.

As appreciated by those of ordinary skill in the art, concerns regarding the safety of growth factors, such as systemic absorption, must be taken into account when used as a means to enhance fibrovascular ingrowth into these implants. At least one previous study showed no evidence of systemic absorption when Rh-βFGF was applied to the rabbit cornea to investigate its role in healing corneal epithelium (Rieck, P., et al., "Recombinant Human Basic Fibroblast Growth Factor (Rh-βFGF) in Three Different Wound Models in Rabbits: Corneal Wound Healing Effect and Pharmacology" Exp Eye Res (1992) 54:987–998); although its behavior when placed within orbital tissues may be different.

Calcium sulfate coating

Donor sclera and other coverings are used by surgeons to provide for several therapeutic advantages, such as to: facilitate attachment of extra-ocular muscles to HA implants, to allow placement of the implant deeply within the orbit, and to prevent tissue breakdown over the rough anterior surface of HA implants. Biocompatible coatings that are used with orbital implants include polylactic acid, polyglycolic acid, and animal tissues such as sclera and fascia. Presently preferred coatings are disclosed in copending U.S. application Ser. No. 08/241,960 filed May 12, 1994 in the name of Arthur C. Perry. As disclosed herein, calcium sulfate was used to coat the HA spheres so as to provide some of the above-described therapeutic advantages of scleral wrappings.

An HA implant manufactured with a smooth covering that achieves these goals while not impeding vascularization would offer several benefits. For example, the cost of obtaining banked sclera would be saved and surgical time would be reduced, particularly relative to use of autologous sclera. Additionally, concerns of infectivity from donor tissue could be reduced, since some patients have refused to accept an HA implant coated with allogeneic sclera due to even a theoretical risk of virus transmission such as HIV (Dutton, J. J., "Coralline Hydroxyapatite as an Ocular Implant" Ophthalmology (1991) 98:370–7). Although a pre-coated HA implant may not replace the function of sclera or other tissue wrappings as a facile means of attaching the extraocular muscles, some surgeons already routinely attach the muscles directly to the HA, without the use of a scleral covering.

Figure 6:
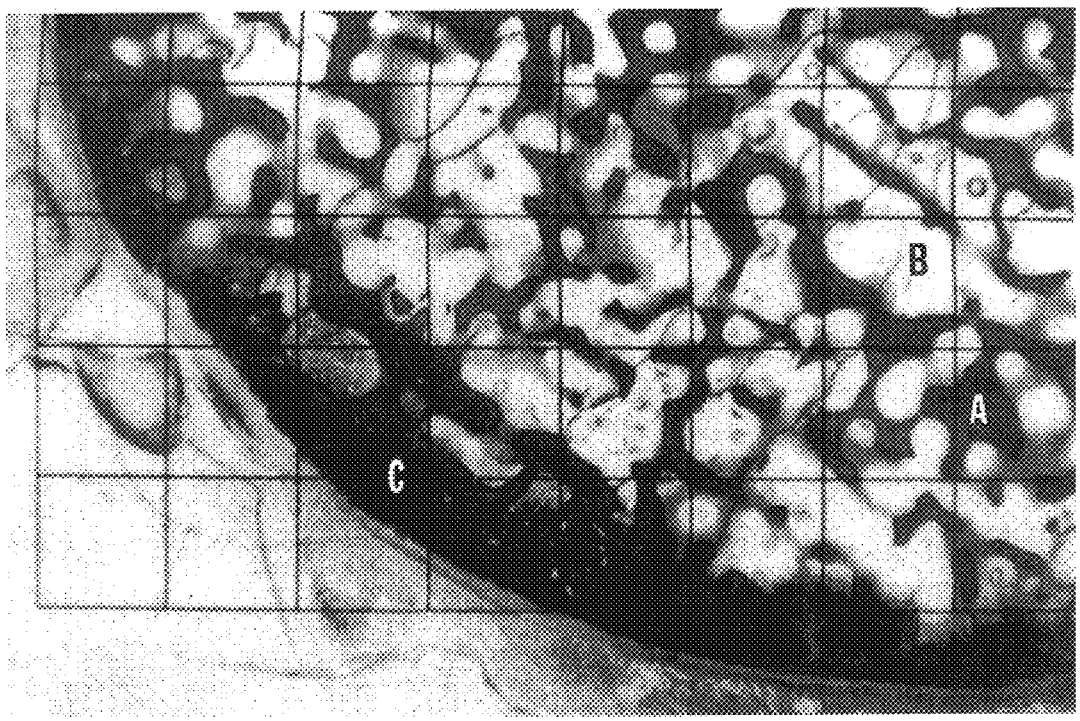
FIG. 6. Cross-sectional specimen of calcium sulfate-coated HA500 explanted two weeks postoperatively. A, hydroxyapatite material; B, pore area; C, residual calcium sulfate. Note lack of fibrovascular tissue in the pore area and the variation in the thickness of the calcium sulfate coating.

The implants disclosed herein were coated with a relatively thick layer of plaster of Paris, i.e., calcium sulfate of about 1 to 1.5 mm thickness. The calcium sulfate coating was still visible at the time of explantation in all cases (FIG. 6). While the material appeared to be well tolerated by the rabbit orbit, two of the calcium sulfate-coated HA implants were lost in the present studies and were presumed to have been exposed and extruded prior to harvesting. The orbital tissues in these rabbits were otherwise healthy in appearance.

Although the calcium sulfate-coated implants did not show significantly lower degrees of fibrovascular ingrowth, the loss of 2 specimens may have affected the statistical power of these results, as visual inspection showed some inhibition of ingrowth. Calcium sulfate coating may still be useful, although thinner layers of calcium sulfate may better achieve desired effects. Additionally, a more-controlled method of application of the coating may be desirable to minimize infections and to ensure the desired thickness can be achieved.

The present data regarding fibrovascular ingrowth is relevant due to its status as a prerequisite of complete integration of porous ocular implants, and because it may be necessary to achieve the complete cosmetic and psychological rehabilitation of an anophthalmic patient, since only a fully vascularized implant can accommodate a motility/support peg.

EXAMPLES

The present examples evaluated the rate and degree of fibrovascular ingrowth in common porous ocular implants as a function of material composition, porosity, treatment with growth factors, and the application of a calcium sulfate (Plaster of Paris) coating.

The present results indicated that smaller pore sizes, minimal physical barriers to ingrowth, and active growth induction by means of growth factors are means of achieving the speed and level of ingrowth needed to achieve the best surgical result and patient satisfaction with porous ocular implants. Particularly surprising was that smaller pore sizes led to enhanced fibrovascular ingrowth.

Example 1
Surgical Enucleation

The animals involved in the studies regarding the present invention were procured, maintained, and used in accordance with the *Animal Welfare Act of* 1966, as amended, and the *Guide for the Care and Use of Laboratory Animals* prepared by the Institute of Laboratory Animal Resources, National Academy of Sciences—National Research Council, as required by SECNAVINST 3900.38B.

Enucleation of the right eye was performed on 81 New Zealand white rabbits averaging 3 kg in weight. Intramuscular anesthesia was administered with 50 mg/kg of Ketamine and 5 mg/kg of Xylazine. The rabbits were also given an IM dose of 0.25 cc of penicillin G. The peri-orbital fur was shaved and the right eye and peri-orbital area were prepped with Betadine solution. A retrobulbar injection of Xylocaine 1% with epinephrine 1:100,000 was given and the surgical site was draped in a sterile fashion.

Following a complete peritomy, the extraocular muscles were tagged with double-armed 5-0 Vicryl suture and were then released from the globe. Muscles were isolated in the infer-nasal quadrant and the supero-lateral quadrant. Upon close inspection, the muscle complex in the supero-lateral quadrant appeared to be composed of two muscles, i.e., a rectus muscle with an attached oblique muscle. The globe was enucleated and pressure was applied to the posterior orbit for hemostasis.

Example 2
Calcium Sulfate Coating

To control the level of calcium sulfate infiltration into the pores, the coralline HA implants were filled with water and frozen prior to application of the calcium sulfate. All implants, except those treated with Rh-βFGF, were sterilized by autoclaving prior to implantation. The Rh-βFGF-treated implants were autoclaved prior to the application of the growth factor in a sterile solution.

Example 3
Surgical Implantation of the Various Implants

Twelve-millimeter ocular implants were prepared for implantation in all cases. A previous study found that 14-mm implants resulted in high rates of exposure (Rubin, P. A., et al., "Comparison of Fibrovascular Ingrowth into Hydroxyapatite and Porous Polyethylene Orbital Implants" *Ophthalmic Plast Reconstr Surg* (1994) 10:96–103), probably due to the small size of the rabbit orbit (J. K. Popham, personal communication, 1995).

All implants were immersed in a 20-mg/ml solution of gentamicin prior to implantation, except for those treated with fibroblast growth factor (Rh-βFGF), which was in a sterile solution. Rh-βFGF was obtained from the Department of Cell Biology, Scripps Research Institute, La Jolla, Calif. It was stored at −80° C. and was passed over an endotoxin column to remove bacterial endotoxin before dilution to a concentration of 10 μg/ml. The concentration was verified by a protein assay and spectrophotometry.

The implants were separated by type and placed in sterile 30-ml syringes, which were then filled with enough solution to completely immerse the implant. Each syringe was capped, the plunger was withdrawn to create a mild vacuum, and the barrel was agitated to release residual air from the implant. The implants were incubated overnight at 4° C. Prior to implantation, the implants were gently rinsed twice with sterile PBS.

All implants were supplied by their respective manufacturers. The calcium sulfate and Rh-βFGF treatments were applied as described herein.

Each 12-mm implant was placed in the center of the orbit between the muscles, and the muscles were sutured to each other over the anterior aspect of the implant. Since all implants were placed unwrapped (i.e., were not within a scleral shell), sterile plastic sleeves were created around the implants, fashioned from surgical drapes or gloves, to facilitate insertion of the implants deeply into the orbit. After the implant insertion, the sleeve material was removed, the conjunctiva was closed meticulously with 5-0 Vicryl suture, standard ophthalmic antibiotic ointment was applied to the orbit and, the lids were sutured together with at least one 5-0 Vicryl suture to allow instillation of ointment postoperatively. The rabbits were individually caged following recovery from anesthesia and each was observed closely during the first postoperative week. Antibiotic ophthalmic ointment was applied to the orbit daily during the first postoperative week.

Example 4
Surgical Explantation

For explantation, the rabbits were sacrificed at the predetermined intervals with intramuscular Ketamine and Xylazine, followed by 2.5 ml of intra-cardiac beuthanasia D. The implants and surrounding tissues were removed and fixed in Formalin. Each specimen was then soaked in water, dehydrated in alcohol, vacuum infiltrated, and then imbedded in methyl methacrylate.

Example 5
Specimen Analysis

The specimens were cut through the center into 1- to 2-mm sections using a wet diamond band saw. The slices were mounted on slides, recut using the sandwich method, and ground down to a thickness of approximately 200 μm. All specimens were stained using the fibrin stain of Ladewig.

The sections were examined at a magnification of 50× using an overlying 1-mm grid. Each 1-mm increment of depth (level) from the edge of the implant was measured at 4 different quadrants by 2 investigators, for a total of 8 measurements per level, with the exception of the innermost level (the intersection of the axes) which was measured twice.

Figure 1:
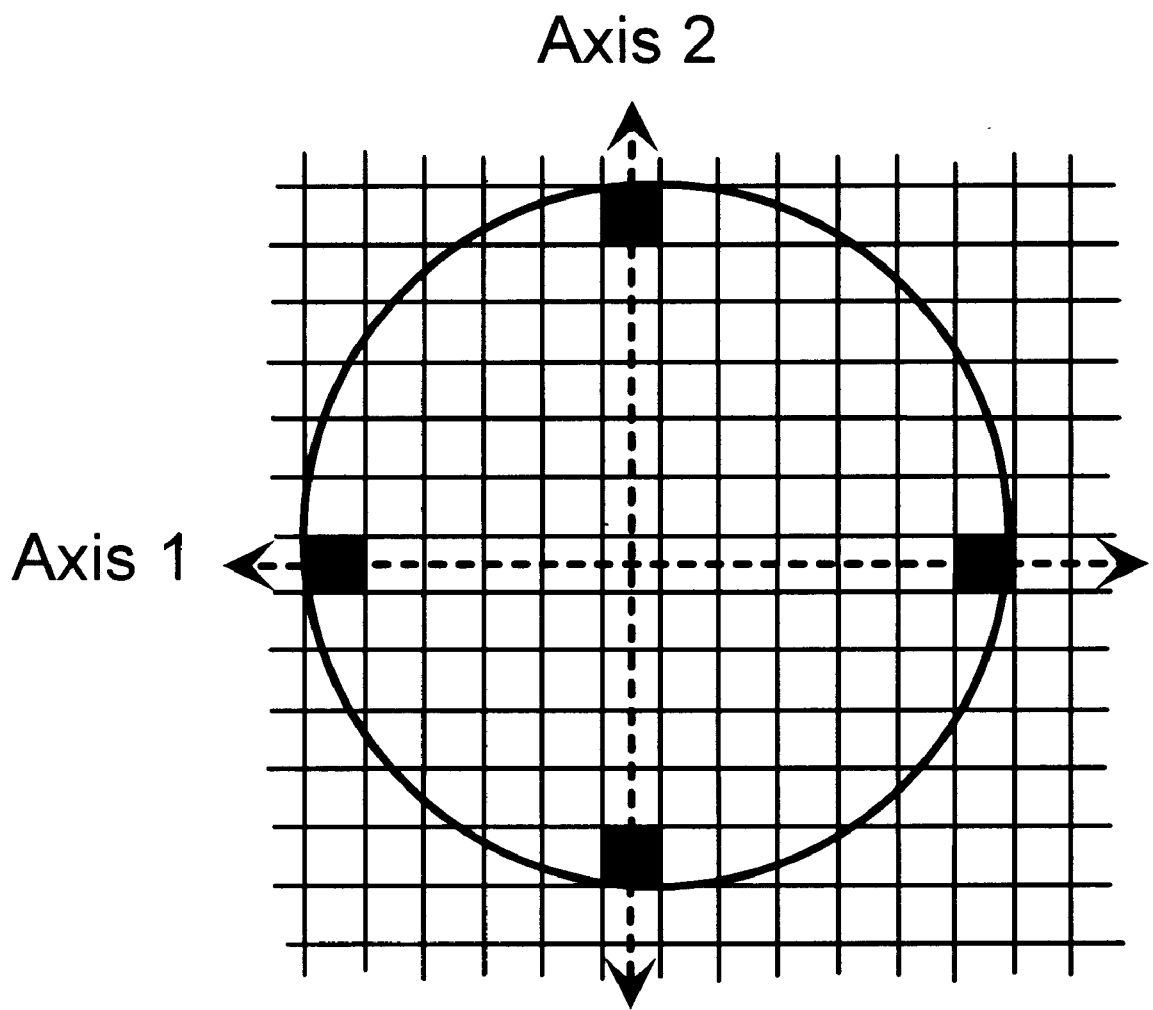
FIG. 1. A schematic representation of Grid Measurement System. Assessment of fibrovascular ingrowth for each 1-mm of depth from the edge of the specimen was made by visually estimating the percentage of tissue within any pores falling within a given grid.
Figure 2:
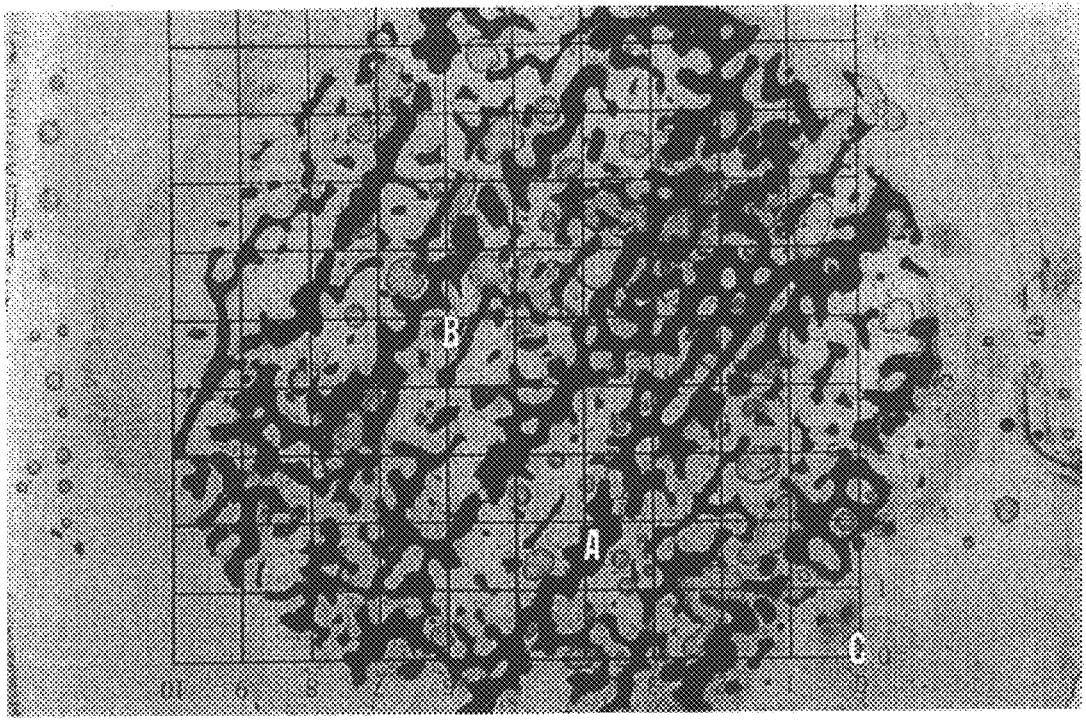
FIG. 2. Cross-sectional specimen of HA500 explanted two weeks postoperatively. A, hydroxyapatite material; B, pore; C, grid. There was a lack of significant fibrovascular tissue within the available pore space. This specimen was graded $\leq 25\%$ ingrown.

Two investigators independently characterized each section at 1-mm intervals (grids) along two perpendicular axes through the center of the implant (FIG. 1), and each investigator estimated the fibrovascular ingrowth in each grid according to the following scale: 0%, ≦25%, ≦50%, ≦75%, and ≦100% of available pore space. For example, a 1×1-mm grid containing some available pore area with no evidence of tissue ingrowth was graded 0%, while an area containing even one cell or tissue fiber was graded ≦25% (FIG. 2).

The inter-investigator assessments were consistent (correlation coefficient 0.935) throughout the investigation ($p<0.0001$). The assessments for the eight data points in each level were averaged to derive the percent-ingrowth per level. The percent-ingrowth for all levels within an implant were averaged to derive the percent-ingrowth per implant type (see Table 3). Statistical differences in the degree of fibrovascular ingrowth among the implant types was determined using a 3-way analysis of variance.

Example 6
Results Following Surgical Explanation

Table 1 shows the breakdown of implant types, treatments and number of implants evaluated.

TABLE 1

Implant type and treatment

| IMPLANT TYPE | NUMBER | NUMBER EXTRUDED | NUMBER EVALUATED |
|---|---|---|---|
| HA200 | 12 | 0 | 12 |
| HA200 GF | 9 | 0 | 9 |
| HA500 | 12 | 1 | 11 |
| HA500 GF | 9 | 0 | 9 |
| HA500 CS | 9 | 2 | 7 |
| PP | 12 | 0 | 12 |
| PP GF | 9 | 0 | 9 |
| SynHA | 9 | 0 | 9 |

Legend:
HA200, reported 200 μm-porosity coralline hydroxyapatite; HA500, reported 500 μm-porosity coralline hydroxyapatite; PP, porous polyethylene; SynHA; synthetic porous hydroxyapatite; GF, growth factor-treated; CS, calcium sulfate-coated.

Three of each of the implants treated with growth factor (HA200 GF, HA500 GF, PP GF) were explanted at intervals of 1, 2, and 4 weeks to assess fibrovascular ingrowth. The same implant types without growth factor (controls) were harvested at 1, 2, 4, and 8 weeks. The synHA implants and those coated with calcium sulfate were harvested at 2, 4, and 8 weeks (see Table 2). Three of the HA500 implants (2 HA500CS, 1 HA500) were not present at the time of harvesting and were presumed to have been extruded.

TABLE 2

Schedule of Explanation and Numbers Explanted, by Implant Type and Treatment

| Implant Type | Week 1 | Week 2 | Week 4 | Week 8 |
|---|---|---|---|---|
| HA200 | 3 | 3 | 3 | 3 |
| HA200 GF | 3 | 3 | 3 | 0 |
| HA500 | 3 | 2 | 3 | 3 |
| HA500 GF | 3 | 3 | 3 | 0 |
| HA500 CS | 0 | 3 | 2 | 2 |
| PP | 3 | 3 | 3 | 3 |
| PP GF | 3 | 3 | 3 | 0 |
| SynHA | 0 | 3 | 3 | 3 |

Exposure and Extrusion—At the time of explanation, two calcium sulfate-coated HA500 implants and one uncoated HA500 implant were absent and were presumed to have completely extruded from the orbit after the first postoperative week.

Of the implants present during explantation, 8 of 79 (10.1%) showed evidence of exposure. Exposure was only noted in the HA implants, as follows: 3 HA500, 3 calcium sulfate-coated HA500, and 2 HA200.

Inflammation and Infection—Most of the 81 rabbits demonstrated some thick, white conjunctival discharge from the orbit in the early postoperative period, which cleared spontaneously. In one rabbit, the discharge continued beyond this period but was responsive to additional applications of ointment. None of the rabbits showed signs of chronic orbital infection.

Most (56%) of the orbits containing implants treated with growth factor showed elevated levels of edema and erythema of the lids and peri-orbital tissues during the first 72 hours postoperatively. The level of inflammation was characterized as follows: 9 moderate (PP, 5; HA500, 4) and 6 severe (PP, 2; HA500, 4). None of the HA200 growth factor-treated implants were associated with elevated levels of inflammation. By postoperative day 3, all of the growth factor rabbits showed normal levels of inflammation and none showed signs of infection.

Notably, a significant difference ($p=0.027$) was found between the level of ingrowth in HA200 and HA500 implants, with the HA200 showing more complete ingrowth. This finding was surprising in view of disclosures regarding the impact of porosity on ingrowth. Previously, it had been reported that implants with larger pores would achieve better ingrowth relative to implants with smaller pores.

Implants treated with growth factor showed significantly greater ($p=0.014$) fibrovascular ingrowth than untreated implants.

Implants coated with calcium sulfate showed less ingrowth than uncoated implants, although the difference did not reach statistical significance ($p=0.055$).

There was a significant difference ($p=0.001$) in ingrowth between the 4 time periods (1 wk, 2 wks, 4 wks, 8 wks) in which the implants were explanted. In all cases, except in the case of PP during week 2, and in 3 instances of extruded implants which restricted the number of data points in a particular cell to 2 implants (see Table 3), more ingrowth was noted with each successive week.

TABLE 3

Percent-ingrowth per implant as a function of material composition, porosity, growth factors, and coatings.

| Implant Type | Week 1 | Week 2 | Week 4 | Week 8 |
|---|---|---|---|---|
| HA200 | 60.6 | 64.9 | 78.5 | 91.3 |
| HA200 GF | 44.5 | 69.3 | 100.0 | NA |
| HA500 | 54.7 | 35.2 [n = 2] | 66.0 | 82.8 |
| HA500 GF | 61.6 | 81.8 | 79.3 | NA |
| HA500 CS | NA | 35.8 | 62.8 [n = 2] | 41.9 [n = 2] |
| PP | 73.8 | 58.3 | 82.9 | 90.5 |
| PP GF | 76.0 | 81.1 | 85.4 | NA |
| SynHA | NA | 53.8 | 64.3 | 86.6 |

Example 7
Pore Size Calculations

Previously, it has been reported that the HA 200 implants had pores sized at 200 micrometers, and that the HA 500 implants had pores sized at 500 micrometers. To confirm these pore sizes, and to determine the pore sizes of the synthetic HA (SynHA) and the porous polyethylene (PP), the following protocol was undertaken. Samples of materials were photographed in a scanning electron microscope (SEM) (Leica STEREOSCAN 400®, Leica, Inc., Deerfield, Ill.). Coralline hydroxyapatite (e.g., HA200 and HA500) has an anisotropic structure. Because of this anisotropy, these samples were prepared for analysis by grinding both parallel and transverse to the long axis of the pore structure. Synthetic HA has a generally isotropic structure. Porous polyethylene is known to have a radial pore structure gradient (see, e.g., Klawitter, J. J. *An Evaluation Bone Growth into Porous High Density Polyethylene J. Biomed. Mater Res.* 10:311–323 (1976)) Accordingly, only the exterior surfaces of the porous polyethylene samples were evaluated.

Photographs of all samples were enlarged a defined amount, and cross-sections of pores were measured manually. The calibration scale printed on the photograph by the SEM was used to convert the measurements to pore dimensions. The longest dimension and the shortest dimension of each pore in the plane of the surface were determined. The two measurements were averaged to obtain a measurement of each pore. The mean of all measured pore sizes was calculated, and a histogram of pore size distribution was prepared for each implant-type measured.

FIG. 7 depicts a histogram of pore size measurements for transverse sections of the HA 200 samples. Forty samples were measured in this plane. The mean pore size was 64 micrometers.

FIG. 8 depicts a histogram of the pore size measurements from longitudinal sections of the HA 200 implants. Forty-three specimens were examined in this plane. The mean pore size was 89 micrometers.

FIG. 9 depicts a histogram for the pore size measurements of HA 500 implants taken along transverse sections. Fifty-eight specimens were examined in this plane. The mean pore size for these measurements was 262 micrometers.

FIG. 10 depicts a histogram of pore size measurements taken from longitudinal sections of HA 500 implants. Fifty-four specimens were examined in this plane. The mean pore size from these specimens was 220 micrometers.

FIG. 11 depicts a histogram of pore size measurements for the implants of porous polyethylene. These pore size measurements were taken at the surface of the implants. Twenty-one specimens were examined. The mean pore size was 563 micrometers.

FIG. 12 depicts a histogram for the pore size measurements taken from synthetic hydroxyapatite implants. Fifty-two specimens were examined. The mean pore size for these samples was 220 micrometers.

It was a surprising finding that the pore size data for the coralline hydroxyapatite implant differed so significantly from what was reported to be the approximate pore size for these materials. Moreover, the newly determined pore size information taken together with the data for fibrovascular ingrowth for the various samples, manifested the particularly surprising finding that enhanced fibrovascular ingrowth took place for hydroxyapatite implants (HA 200) having a mean pore size of 64 micrometers in a transverse section and 89 micrometers in longitudinal section. Taking an average of the transverse and longitudinal pore size determinations for this material, it was found that enhanced fibrovascular ingrowth took place in a material having an average pore size of approximately 77 microns. Previously reported studies directed and encouraged selection of implant materials having substantially larger pore sizes than such samples.

Closing

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to equivalent to those described herein can be used in the practice or testing of the invention, the preferred methods and materials are now described. All publications or applications mentioned herein are fully incorporated by reference herein.

What is claimed is:

1. A non-polyethylene porous orbital implant structure for implantation into the orbital cavity of a mammal comprising pores having a mean size of less then 200 micrometers.

2. The porous structure of claim 1, wherein said structure comprises a ceramic.

3. The porous structure of claim 1, wherein said structure comprises hydroxyapatite.

4. The porous structure of claim 1, wherein said structure consists essentially of a ceramic.

5. The porous structure of claim 1, for implantation into the orbital cavity of a mammal comprising pores having a mean size of from 50 to 150 micrometers.

6. The porous structure of claim 5, for implantation into the orbital cavity of a mammal comprising pores having a mean size of from 60 to 90 micrometers.

7. The porous structure of claim 6, for implantation into the orbital cavity of a mammal comprising pores having a mean size of from 75 to 85 micrometers.

8. The porous structure of claim 7, for implantation into the orbital cavity of a mammal comprising pores having a mean size of about 77 micrometers.

9. The porous structure of claim 1 further comprising a growth factor.

10. The porous structure of claim 9, wherein the growth factor is recombinant human basic fibroblast growth factor beta.

11. The porous structure of claim 1 further comprising a biocompatible coating.

12. The porous structure of claim 11, wherein the coating is calcium sulfate, polylactic acid, polyglycolic acid, or animal tissue.

13. A surgical method for placing an implant into a mammal who has had an ocular enucleation, evisceration or who needs implant replacement, whereby the implant obtains rapid ingrowth of connective and vascular tissues, said method comprising:

selecting a non-polyethylene porous ocular implant comprising pores with a mean size of less than 200 micrometers; and placing the implant into an orbital cavity of a mammal.

14. The method of claim 13, further comprising a step of burying the implant beneath conjunctival tissues of the mammal.

15. The method of claim 13 further, comprising a step of covering the implant before the placing step.

16. The method of claim 15, wherein the covering step comprises covering the implant with scleral tissue.

17. The method of claim 15, wherein the covering step comprises covering the implant with calcium sulfate, polylactic acid, polyglycolic acid or animal tissue.

18. The method of claim 13, further comprising applying a growth factor to the implant.

19. The method of claim 18, wherein the step of applying a growth factor comprises applying recombinant human basic fibroblast growth factor beta.

* * * * *